United States Patent
Mak

(10) Patent No.: US 9,513,202 B2
(45) Date of Patent: Dec. 6, 2016

(54) VISCOMETER

(71) Applicant: Alex Mak, Canton, MA (US)

(72) Inventor: Alex Mak, Canton, MA (US)

(73) Assignee: BEL Legacy Corporation, Middleborough, MA (US)

( * ) Notice: Subject to any disclaimer, the term of this patent is extended or adjusted under 35 U.S.C. 154(b) by 483 days.

(21) Appl. No.: 13/961,394

(22) Filed: Aug. 7, 2013

(65) Prior Publication Data

US 2014/0047904 A1 Feb. 20, 2014

Related U.S. Application Data

(60) Provisional application No. 61/682,980, filed on Aug. 14, 2012.

(51) Int. Cl.
*G01N 11/14* (2006.01)

(52) U.S. Cl.
CPC ..................... *G01N 11/14* (2013.01)

(58) Field of Classification Search
CPC ........................................ G01N 11/14
USPC ........... 73/54.01, 54.23, 54.28, 54.32, 54.33, 73/862.08, 862.191, 862.321, 73/862.325, 73/862.331; 324/200, 207.11, 324/207.25
See application file for complete search history.

(56) References Cited

U.S. PATENT DOCUMENTS

| | | | |
|---|---|---|---|
| 5,987,970 A * | 11/1999 | Ball | G01N 11/14 73/54.28 |
| 6,691,560 B2 * | 2/2004 | Abnett | G01N 11/14 73/54.28 |
| 6,938,464 B1 * | 9/2005 | Bi | G01N 11/162 73/54.23 |
| 2001/0042400 A1 * | 11/2001 | Boyle | B03C 3/28 73/54.28 |
| 2007/0132447 A1 * | 6/2007 | Reimer | G01L 3/104 324/207.21 |
| 2009/0315541 A1 * | 12/2009 | Zak | B60T 8/171 324/207.2 |
| 2010/0294603 A1 * | 11/2010 | St. Clair | B60T 13/748 188/267 |
| 2011/0164070 A1 * | 7/2011 | Sirmon | G09F 9/33 345/690 |
| 2012/0234107 A1 * | 9/2012 | Pindiprolu | G01N 11/14 73/862.331 |
| 2014/0306692 A1 * | 10/2014 | Santos | G01D 5/145 324/207.2 |
| 2015/0224845 A1 * | 8/2015 | Anderson | B60G 17/019 701/37 |

* cited by examiner

*Primary Examiner* — Hezron E Williams
*Assistant Examiner* — Hoang Nguyen
(74) *Attorney, Agent, or Firm* — Jerry Cohen; John A. Hamilton

(57) ABSTRACT

Viscosity or rheology measuring instrument utilizing Hall Effect or like magnetic coupling with parts mounted on driving and driven rotational assemblies.

15 Claims, 19 Drawing Sheets

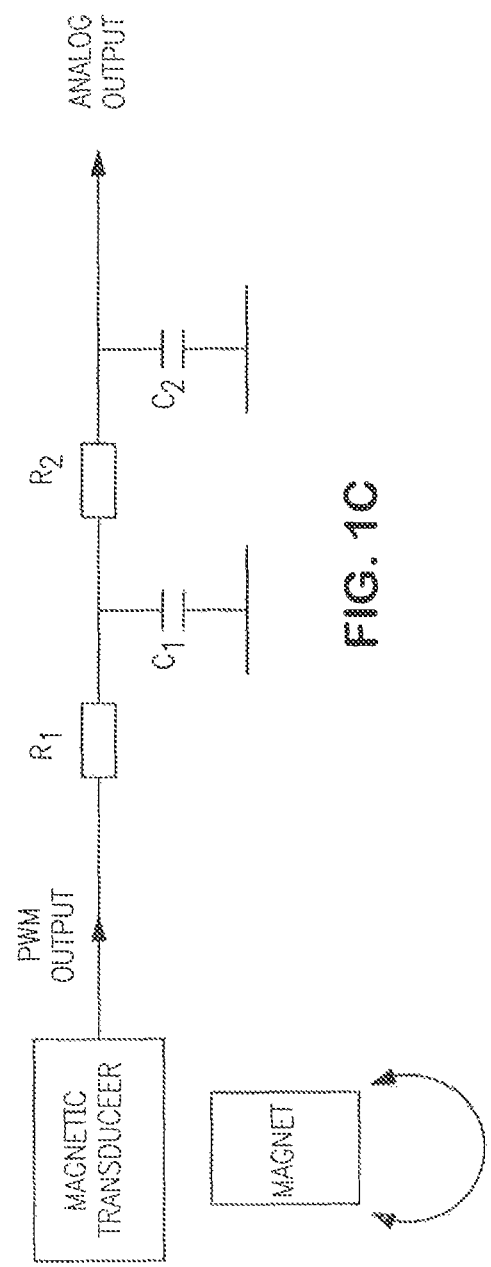

MAGNETIC TRANSDUCER WIRELESS IMPLEMENTATION WITH ROTARY TRANSFORMER & OPTICAL OUTPUT

VISCOMETER

The present invention claims priority from U.S. provisional application 61/682,980 filed 14 Aug. 2012 and is related to PCT application Serial No. PCT/US2012/000502 International Filing Date 5 Oct. 2012. The invention relates to viscometers which rely on a linear or angular displacement of driving and driven motions in a fluent medium where viscosity is to be measured. Many such viscometers lack desired base precision and/or are sensitive to axial alignment variations and variation of temperatures.

FIELD AND BACKGROUND OF THE INVENTION

One of the problems of widely available rotary viscometers is that of temperature drift. For example, the Brookfield Engineering Laboratories, Inc., (BEL) model CAP3000™ cone and plate rotary viscometer with a MSI brand variable inductance transducer has a temperature drift of about −/+2% full scope error over about a −10 to 50° C. range of angular deflection. Coping with axial movement due to e.g. cone tip wear is also an issue in maintaining reliable readings over long durations of instrument use. It is also a need to enable a large angular range for full scale.

There is also a need for continuous reading of viscosity. For instance, some BEL cone and plate viscometers use an optical time base sensing mechanism for angular air placement giving a limited number of readings per revolution (e.g. two) at 0.01 rpm.

It is an object of the invention to provide a greater precision in such viscometer. It is a further object to reduce or eliminate problems arising out of axial orientation issues and/or temperature variations. It is a further object to achieve the foregoing with minimal change to configuration of the viscometer and its electrical circuitry and computer interfacing.

SUMMARY OF THE INVENTION

The objects are achieved by a viscometer constructed with a Hall Effect transducer which can be (a) centered axially, (b) mounted a radial distance from the viscometer axis, (c) provided with extra bearing support and (d) other configurations. Other magnetic transducers can also be used to good effect. The transducer should have multiple sensors in a single thermal environment e.g. multiple sensors on a single die monolithic construction preferably also affording capabilities of signal conditioning, A/D conversion, DSP and interface electronics on the same die.

The magnet and sensor of the Hall Effect transducer are mounted on separate areas of the customary drive shaft and sensing shaft of a rotational viscometer, the latter being suspended from a rotating frame driven by the drive shaft and the sensing shaft being coupled to the drive shaft by one or more torque springs preferably two with each being in spiral form and oppositely coiled. Multiple axially spaced bearings are preferably provided along sensing shaft length and the bearings are mounted from a housing driven by the drive shaft so that there is minimal or no bearing torque drag. A sensing end such as a cone and plate or barrel cylindrical end rotor is installed at the spindle end.

The electrical signal generated by the Hall Effect transducer, usually a digital signal can be converted to analog using simple low pass filters. The analog signal can be extracted by brush and slip ring means affording continuity of signal extraction and the construction as a whole is usable to extract a wide range signal due to a large range angular relative displacement of the sensing and drive shafts. The signal can be maintained as digital, converted to analog e.g. with pulse width moderation output and low pass filters and converted back to digital. Preferably one or both elements of the Hail Effect transducer (sensor and magnet) are set up on the main axis of a rotary viscometer, but radial offset of one or both is also feasible. Further, the driving shaft and sensing shaft are coupled by one or more spiral coil arrays and more preferably multiple arrays (including one or more served by spindled pairs) to avoid a zero shift at high speed. The instrument and transducer cover a wide range and may have relative angular displacements of up to 300 degrees. This is accomplished by a brush/slip ring form or like means of signal extraction.

The new viscometer of the invention is exemplified by preferred embodiments described below with references taken in conjunction with the accompanying drawings in which:

BRIEF DESCRIPTION OF THE DRAWINGS

FIGS. 1-A, and 1A-2 (prior art) show schematically a comparison of the viscometer electronics with a Hall Effect transducer or like transducer with state of the art transducer such as the variable inductance MSI transducer cited above;

FIG. 1C shows schematically a block diagram of the electronics incorporating a rotary transducer and low pass filter circuits;

FIG. 2 shows another viscometer embodiment 10.2 with a coupling 15 connecting two parts of the driving shaft 14A, 14B.

FIG. 3 shows another viscometer with upper and lower half housing configurations as described for FIG. 2 above but uses the on-axis Hall Effect transducer as in FIG. 1.

FIG. 4 shows a viscometer 10.4 similar to FIG. 3 with a modified sensing shaft assembly 28A, spindle 26A, a sensing shaft bearing 30B' and single spiral torque spring 32.

FIG. 5 shows a viscometer 10.5 similar to the viscometer of FIG. 4 but with dual spiral torque springs as in FIG. 1.

FIG. 7 shows linearity within + or −0.1% of full scale range at various temperatures vs. + or −0.25% full scale linearity for the viscometer with MSI transducer;

FIG. 8 shows error vs. x axis displacement (in range of −0.02 to +0.02 in per inch for the viscometer with Hall Effect transducer vs. for the viscometer with MSI transducer);

FIG. 9 shows error vs. x axis displacement (in range of −0.02 to +0.02 in per inch for the viscometer with Hall Effect transducer vs. for the viscometer with MSI transducer);

FIG. 10 shows improvement comparisons for limits on error due to y, z axis deviations;

FIG. 11 shows improvement comparisons for limits on error due to y, z axis deviations;

FIG. 12 shows improvement comparisons for limits on error due to y, z axis deviations FIG. 13 shows test data obtained in implementation of the present invention including performance comparisons with vis-à-vis prior art items FIG. 14 (prior art) shows prior art system error vs. deflection angle performance at various temperatures that may be compared to the performance improvement illustrated in FIG. 6 for an embodiment of the invention.

DETAILED DESCRIPTION OF PREFERRED EMBODIMENTS

Figure 1:
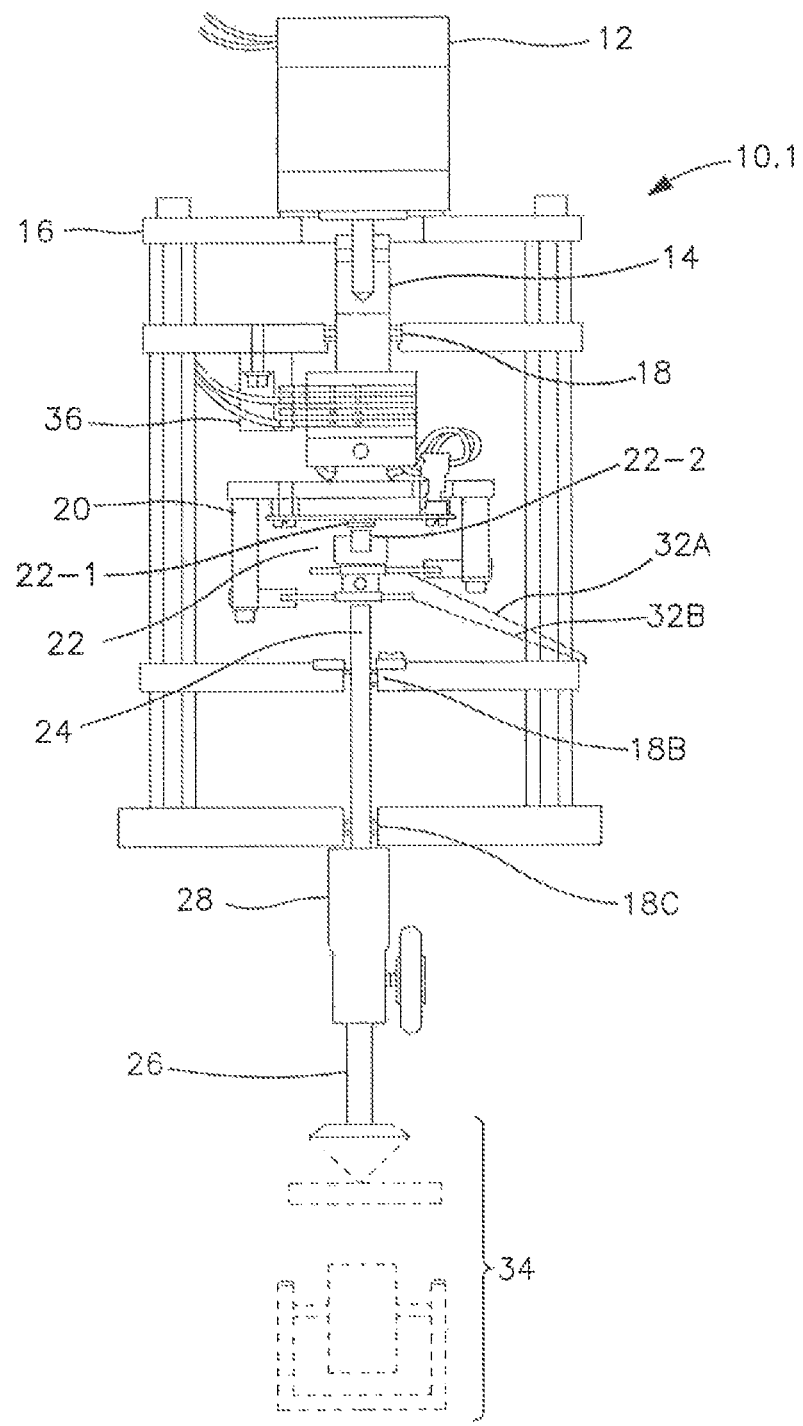
FIGS. 1-5 are side views of several embodiments of the invention in which like parts between embodiments have the same reference numbers.

FIG. 1 shows a viscometer 10.1 comprising a motor 12 (preferably a stepper motor with a flywheel mounted on it) coupled to a driving shaft 14, the drive shaft being mounted from a static frame assembly 16 via a drive housing 18 and drive and sensing shaft bearings, 18B, 18C. A frame extension 20 of the driving shaft mounts one component 22-1 of a Hall Effect transducer 22 which confronts the other component 22-2. One of them (22-2) can be a dramatically magnetized magnet component and the other (22-1) a magnetic sensor with Hall Effect operation. A sensing shaft 24 suspends a spindle 26 via connector coupling 28 and is held from the frame assembly, via bearings 18B and 18C. Two spiral torque springs 32A and 32B couple the sensing shaft to the driving shaft for commonly driven rotation but allowing for angular displacement. They are preferably coiled in opposite directions. Various forms of fluid measuring contact means indicated at 34 can be mounted at the spindle lower end.

Change in viscosity of a measured fluid causes selective angular displacement of the 22-1 and 22-2 components to produce a signal taken out, via brush and slip ring assembly 36. A Hall Effect transducer has a voltage output from a magnetic field pickup (typically a semiconductor crystal) that varies with angular displacement in proportion to the strength of the magnetic field. It can be operated in analog or digital modes, the latter being preferred for modern viscometer usage.

Figures 1, 1A:
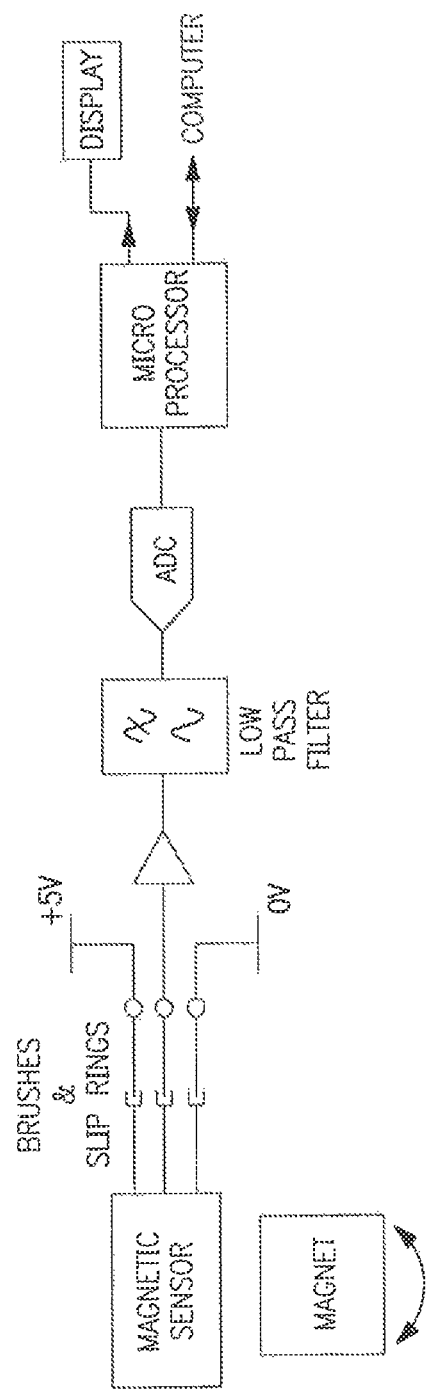
Figures 1, 1A, 2:
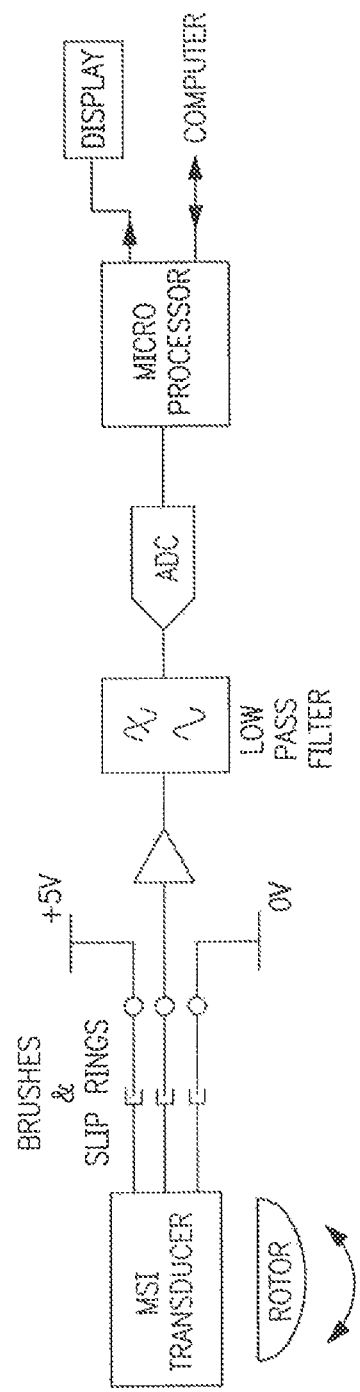

FIGS. 1A and 1A-2 (Prior Art) compare the general control signal readout showing a general similarity of readout with low pass filter, analog-digital-converter (ADC) microprocessor, display and computer or both in the present invention, e.g. as in the embodiment of FIG. 1 with a magnetic sensor or a prior art variable inductance transducer (e.g. MSI) in both instances with brushes and slip rings for signal extraction. Thus it is seen as a significant advantage of the Hall Effect transducer on other like magnetic transducer is that the digital signal can be converted to analog and replace the MSI transducer without any material changes on the electronics design. The same power supply and signal extraction method using brushes and slip rings can be used. The analog signal output range also is compatible with the MSI transducer.

Figure 1B:
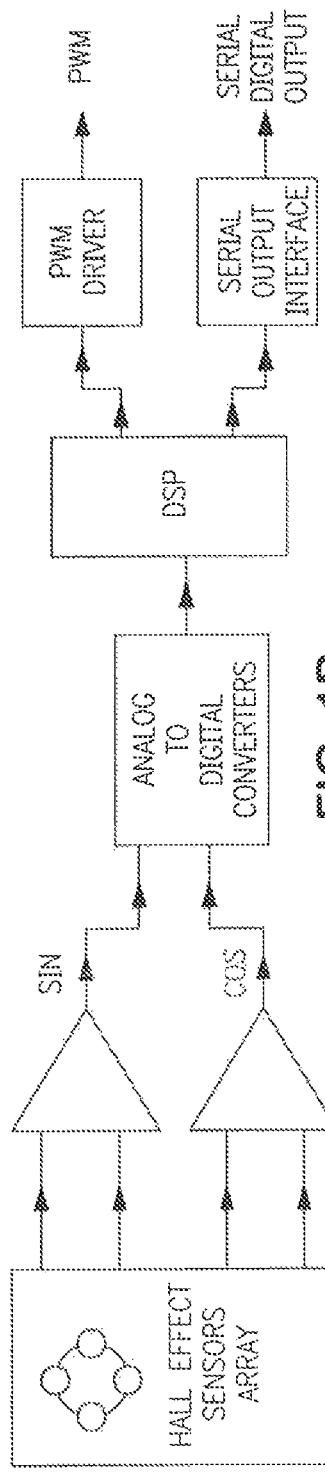
FIG. 1B shows schematically a block diagram of a Hall Effect sensor array to generate differential sine and cosine wave outputs to enable reduced temperature drift.

FIG. 1B is a more particular block diagram of the Hall Effect transducer's sensor and with output amplified for sine (sin) and cosine (cos) readings applied to an analog-to-digital converter and through it to a digital signal processor which provides a pulse width modulated (PWM) signal via a PWM driver and a serial digital output via a serial output interlace. A single Hall Effect sensor construction would have large temperature drift and less tolerance to axial/radial misalignment. The monolithic magnetic transducer has multiple Hall Effect sensors around the magnetic sensing center (e.g. eight) to give differential sine and cosine output to give lower temperature drift and higher sensitivity over the whole revolution with higher axial/radial misalignment tolerance. The sensors outputs are digitized by the analog to digital converter on the same die and a Digital Signal Processor (DSP) calculate the angular displacement. The digital result is available in two digital forms, PWM and serial digital output.

FIG. 1C shows a block diagram means for converting the transducer pulse width module to an analog output, including low pass filters comprising an R-C circuit, of R1, C1, R2, C2 constructed to produce a high enough time constant to reduce output ripple but without being sensitive to viscometer electronic circuit impedances thus reducing temperature sensitive drift from leakage currents where the values are typically

| R1 | 10,000 ohms |
| R2 | 10,000 ohms |
| C1 | 1 microFarad |
| C2 | 1 microFarad |

Figure 1D:
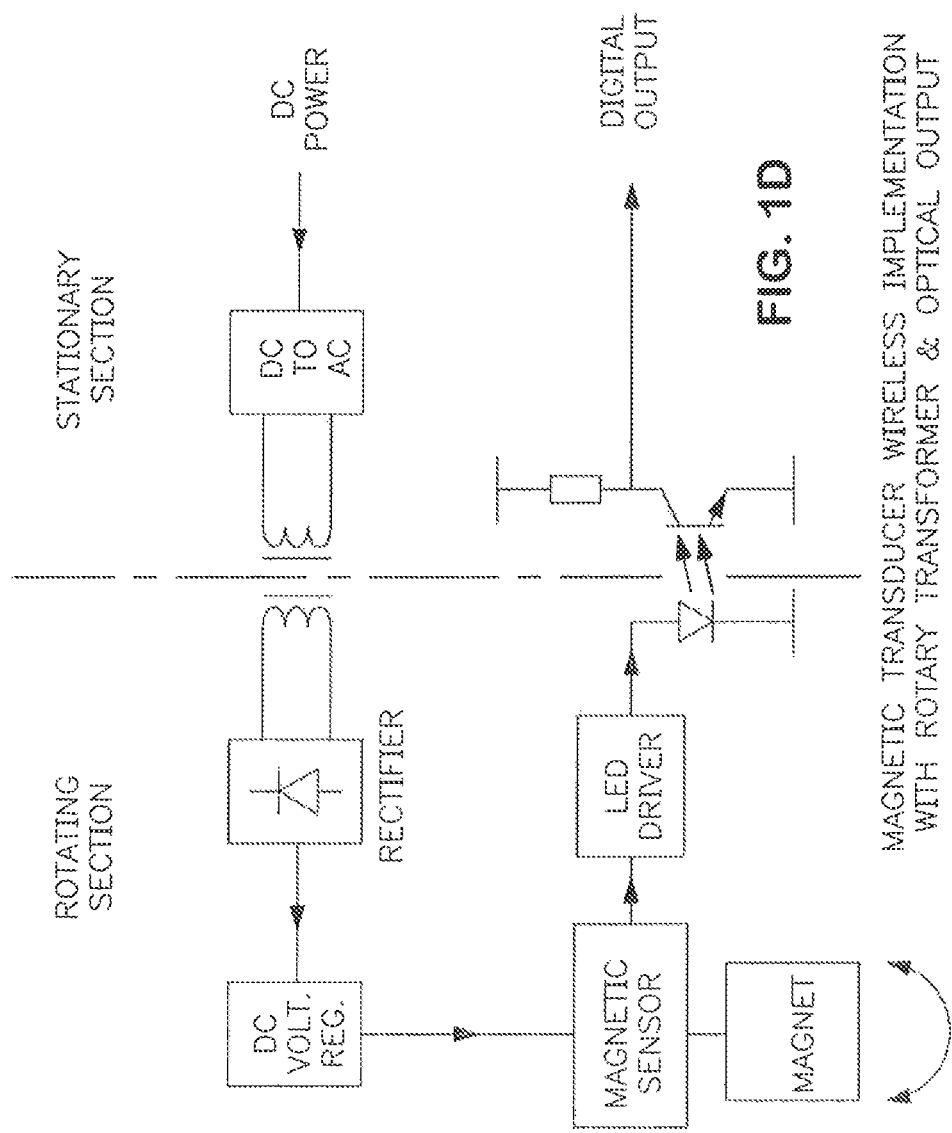
FIG. 1D shows an optical coupling alternative to brush and slip ring signal extraction.
Figure 2:
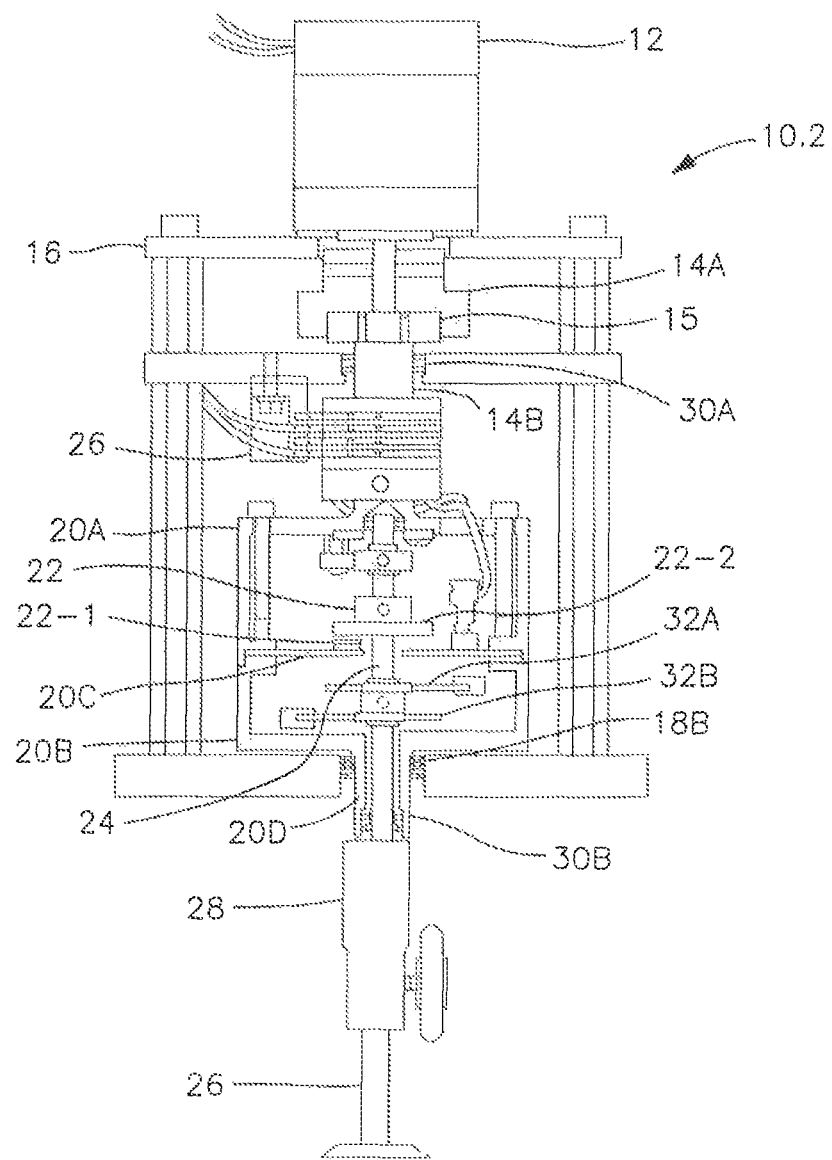

FIG. 1D shows an optical alternative to brush and slip ring signal extraction with a power supply and DC to AC converter in the stationary section of the Hall Effect transducer and a primary transducer cone coupled via its magnetic field to the moving magnet which has the corresponding secondary coil. This non-contact wireless solution can increase reliability and the life of the viscometer. The DC power is converted to AC to drive the rotary transformer and the AC frequency is selected to maximize efficiency for a given transformer and load impedance. The inducted power on the rotation section is rectified and regulated to drive the magnetic transducer. The digital output from the transducer can be used to drive an optical emitting device and a receiver, on the stationary section, to pick-up the optical signal and feed it to the viscometer electronics. Multiple emitters and/or receivers could be used to eliminate line-of-sight issues.

FIG. 2 shows another viscometer embodiment 10.2 with a coupling 15 connecting two parts of the driving shaft 14A, 14B. The drive housing suspended from that shaft has an upper half 20A and lower half 20B, divided by an inwardly extending rib support 20C. The Hall Effect transducer component 22 has a sensor 22-1 that is radially displaced from the instrument axis and its cooperating magnet ring 22-2A is on-axis. The sensing shaft 24 is centered by axially spaced bearings 30A, 30B acting cooperatively with the frame lower half that has a descending cylindrical section with drive bearings 18B and holds sensing shaft bearing 30B. Dual opposite, coiled spiral torque springs 32A and 32B are provided.

Figure 3:
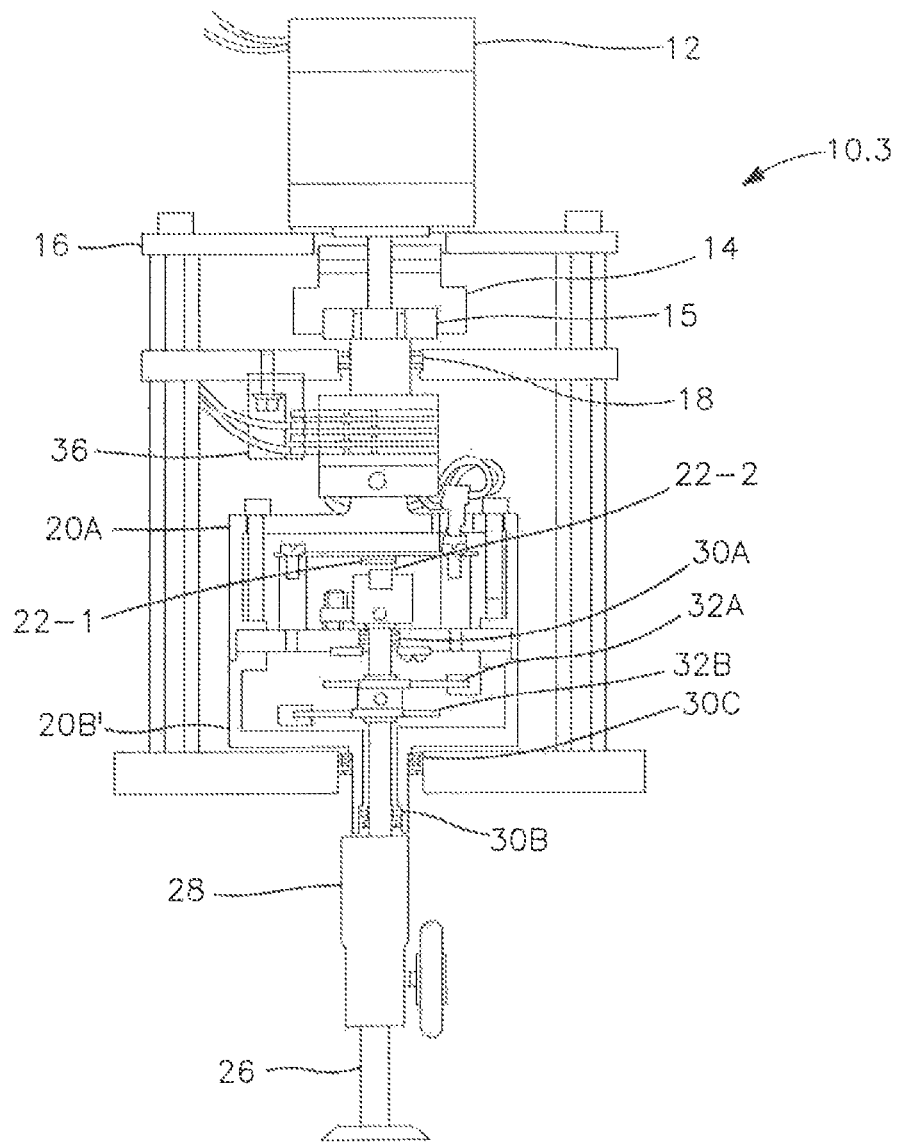

FIG. 3 shows another viscometer with upper and lower half housing configurations as described for FIG. 2 above but uses the on-axis Hall Effect transducer as in FIG. 1.

Figure 4:
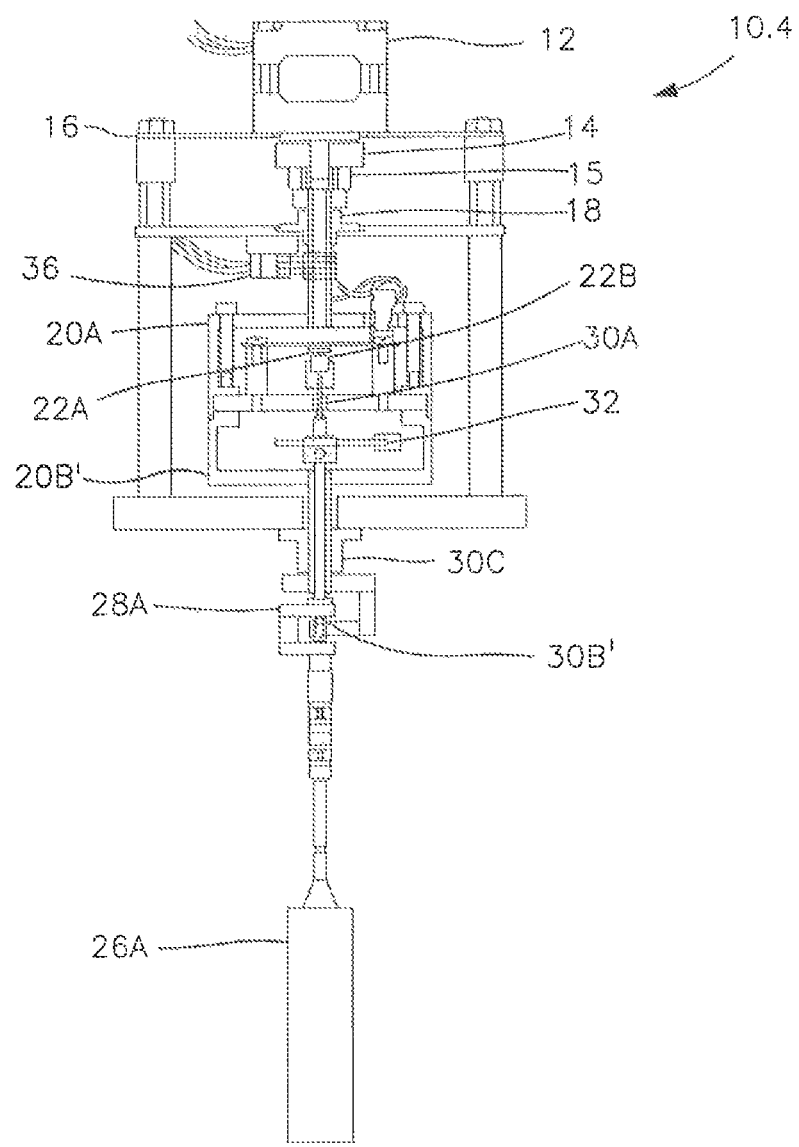

FIG. 4 shows a viscometer 10.4 similar to FIG. 3 with a modified sensing shaft assembly 28A, spindle 26A, a sensing shaft bearing 30B' and single spiral torque spring 32.

Figure 5:
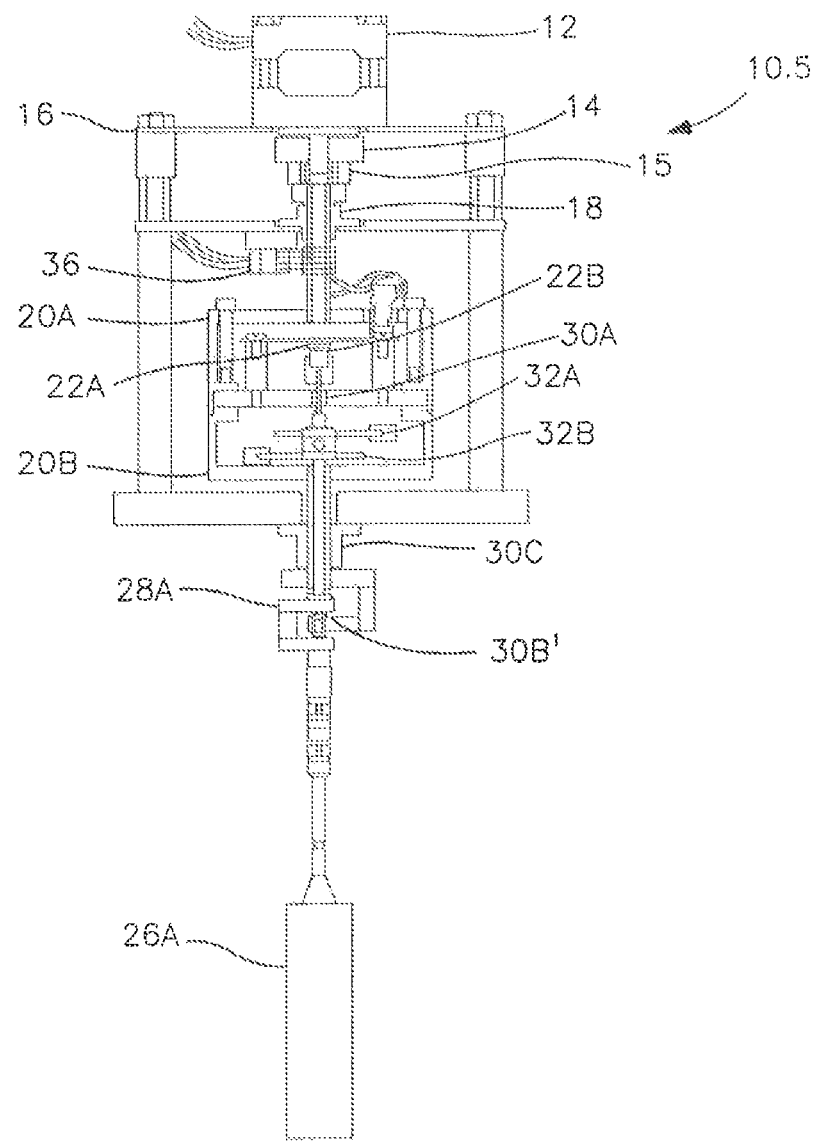

FIG. 5 shows a viscometer 10.5 similar to the viscometer of FIG. 4 but with dual spiral torque springs as in FIG. 1.

Figure 6:
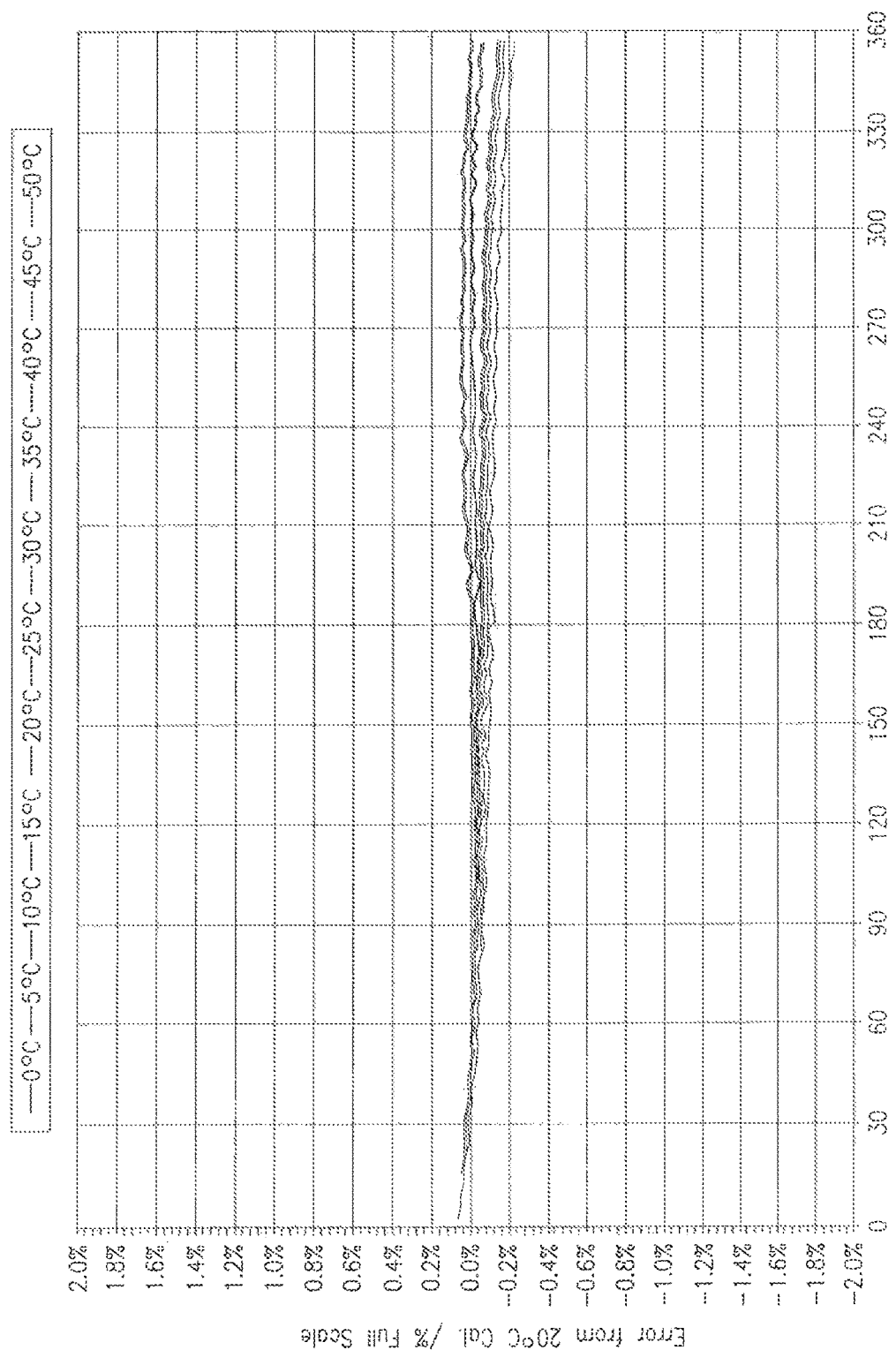
FIGS. 6-13 show test data obtained in implementation of the present invention including performance comparisons with vis-à-vis prior art items; specifically temperature range is shown in FIG. 6 for the viscometer with Hall Effect transducer.
Figure 7:
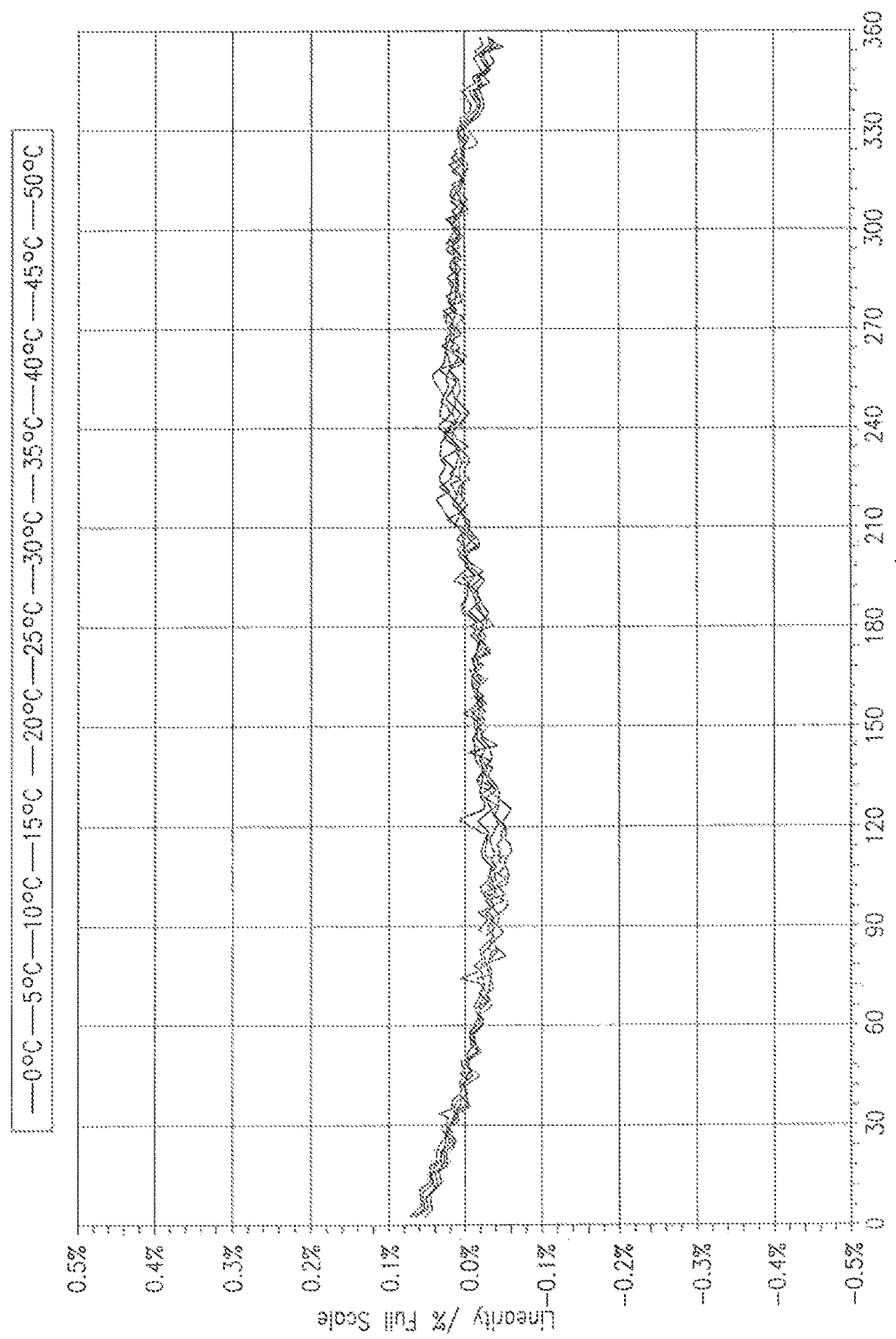

The Hall Effect transducer can be, for example, a model AS5045 from Austria MicroSystems (Unterpremestaetten Austria) or a model MLS 90316 from Melexis Technologies SA (Bevaix, Switzerland). Data sheets for these products can be found at the respective websites http://www.ams.com and http://www.melexis.com. See also, published patent application of M. Schrems et al. (assigned to Austriamicrosystem) no. 20110050210 published Mar. 3, 2011 entitled:

"Vertical Hall Sensor and Method for Manufacturing a Vertical Hall Sensor"; U.S. Pat. No. 7,259,566 B2 to R. Popovic et al. (assigned to Melexis) for "Magnetic Field Sensor and Method for Operating the Magnetic Field Sensor", and the published U.S. patent application of C. Schott (Melexis) published Apr. 24, 2012 for "Vertical Hall Sensor." The disclosures of the above cited items are incorporated in this application by reference as though set out at length herein. One of the Hall Effect sensors described therein (AS5045) was incorporated into conventional Brookfield cone-and-plate and cylinder viscometers, replacing the usual rotary variable inductance differential transformer (MSI model RVIT-Z) of that instrument and in comparative performance tests showed these results:

(a) an error vs. deflection over a 360° range for the viscometer with Hall Effect transducer vs. 75° full scale range for the same viscometer with MSI transducer, indicating under +0.1% -0.2% of full scale error over a 0° C. to 50° C. temperature range as shown in FIG. 6 for the viscometer with Hall Effect transducer:

(b) linearity within + or −0.1% of full scale range at various temperatures vs. + or −0.25% lull scale linearity for the viscometer with MSI transducer; (FIG. 7)

Figure 8:
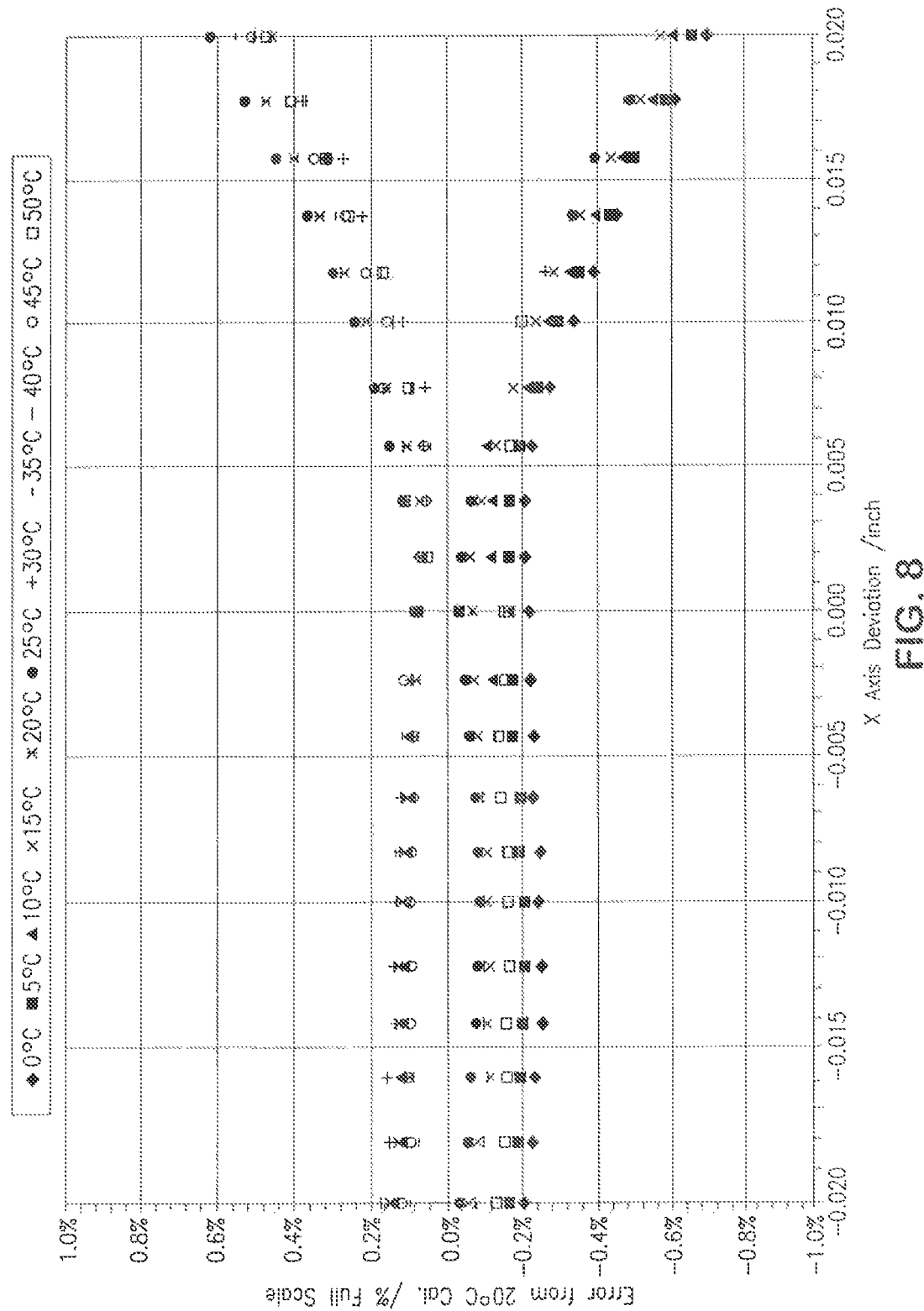
Figure 9:
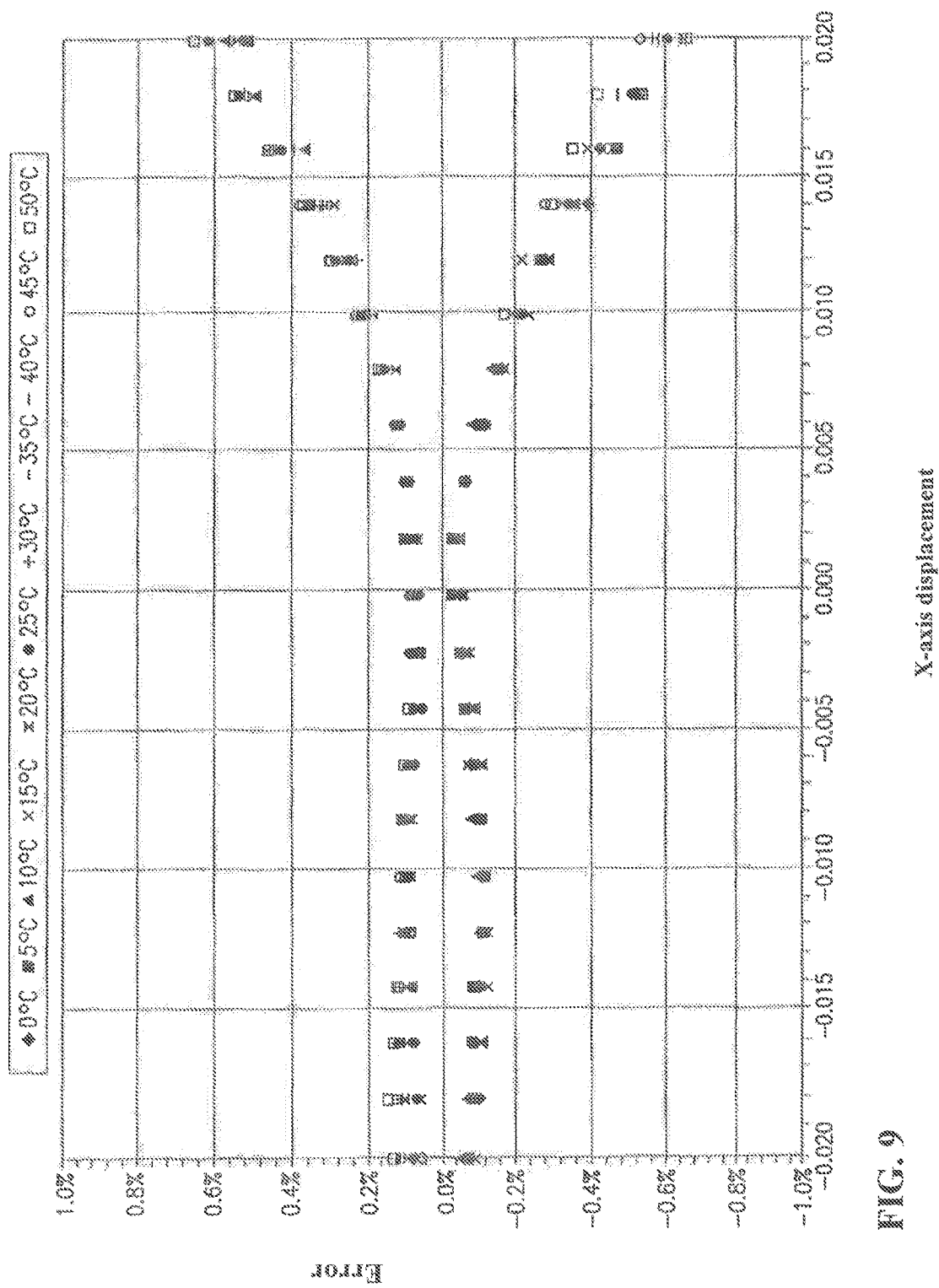
Figure 10:
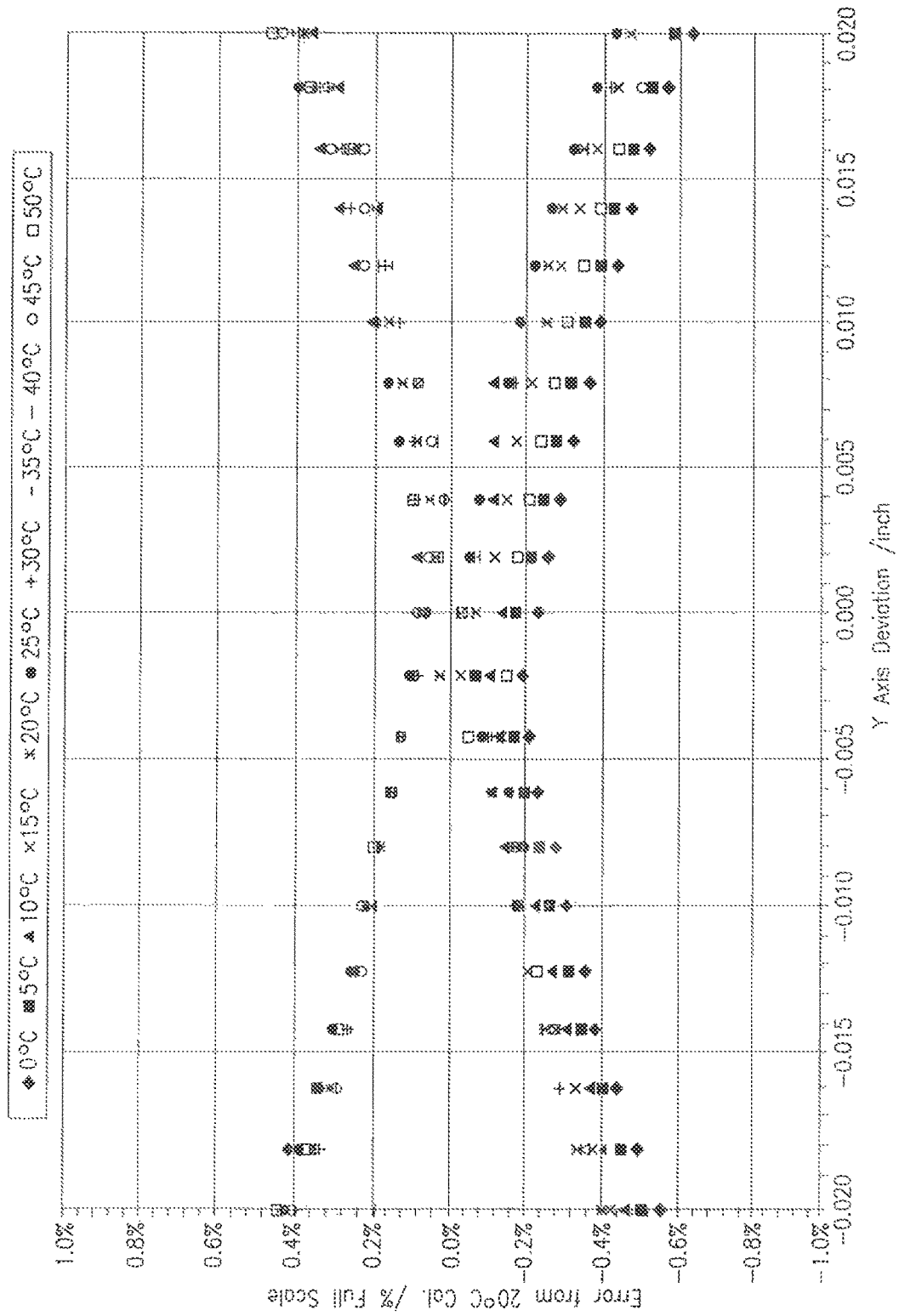
Figure 11:
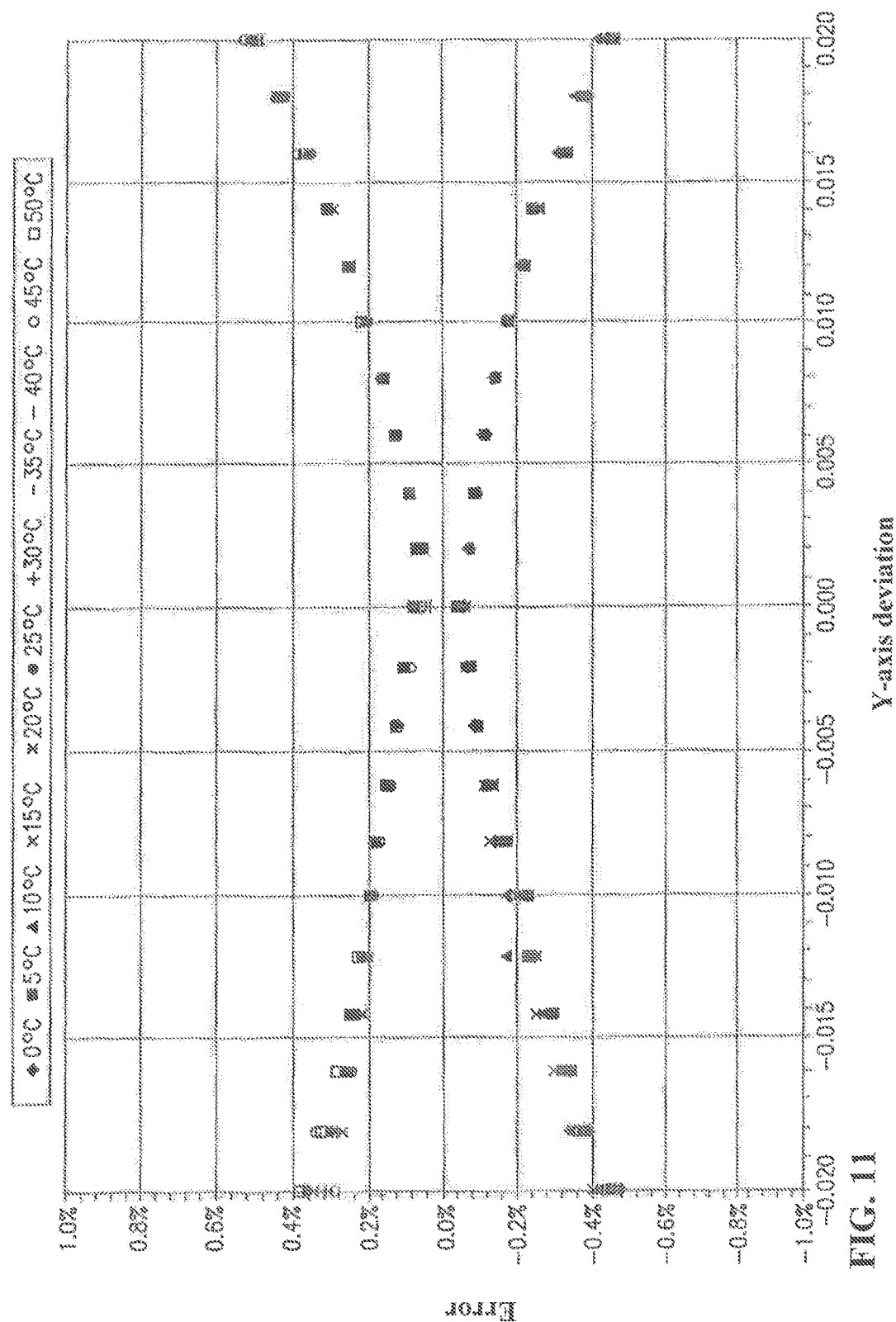
Figure 12:
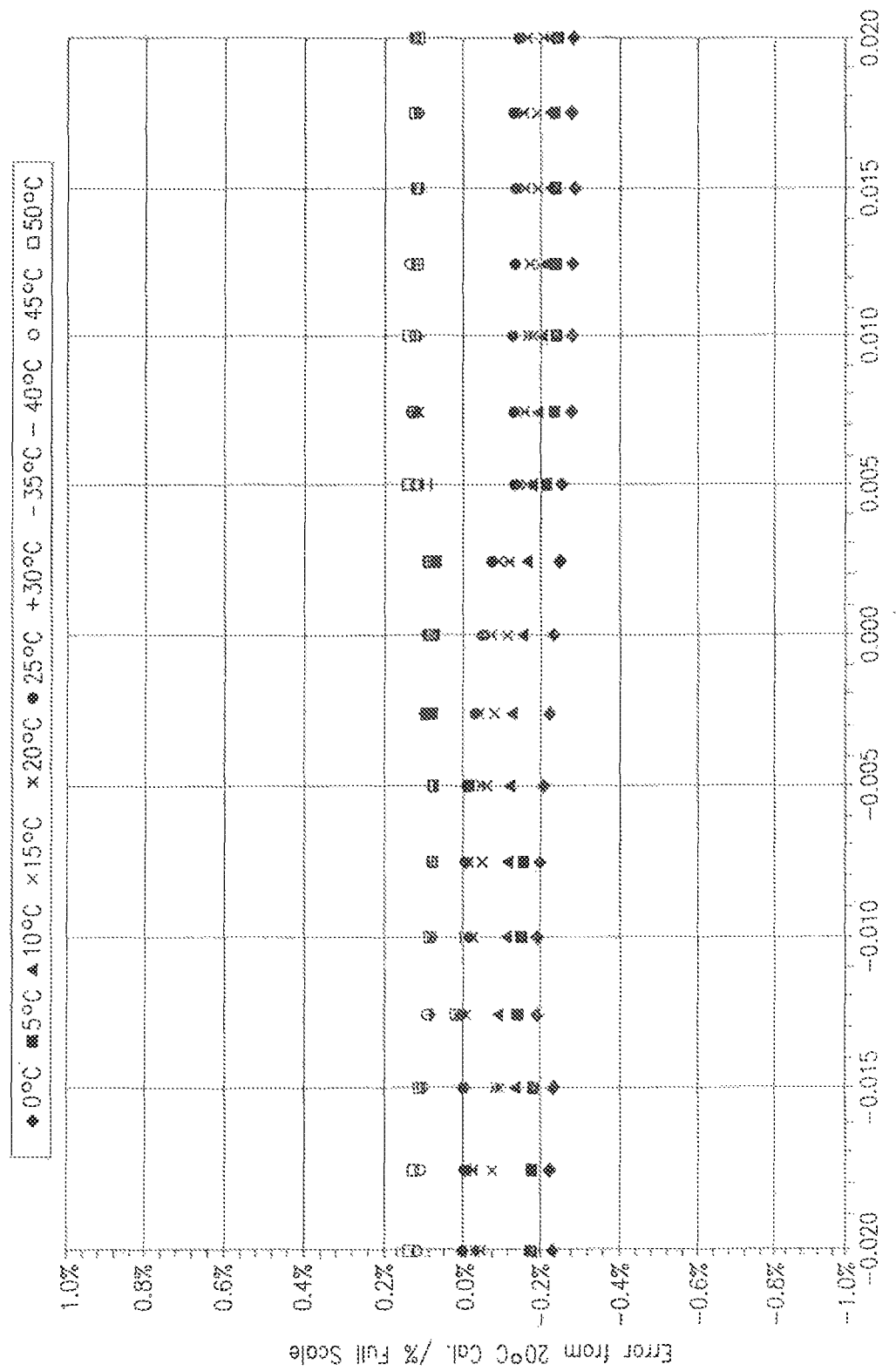
Figure 13:
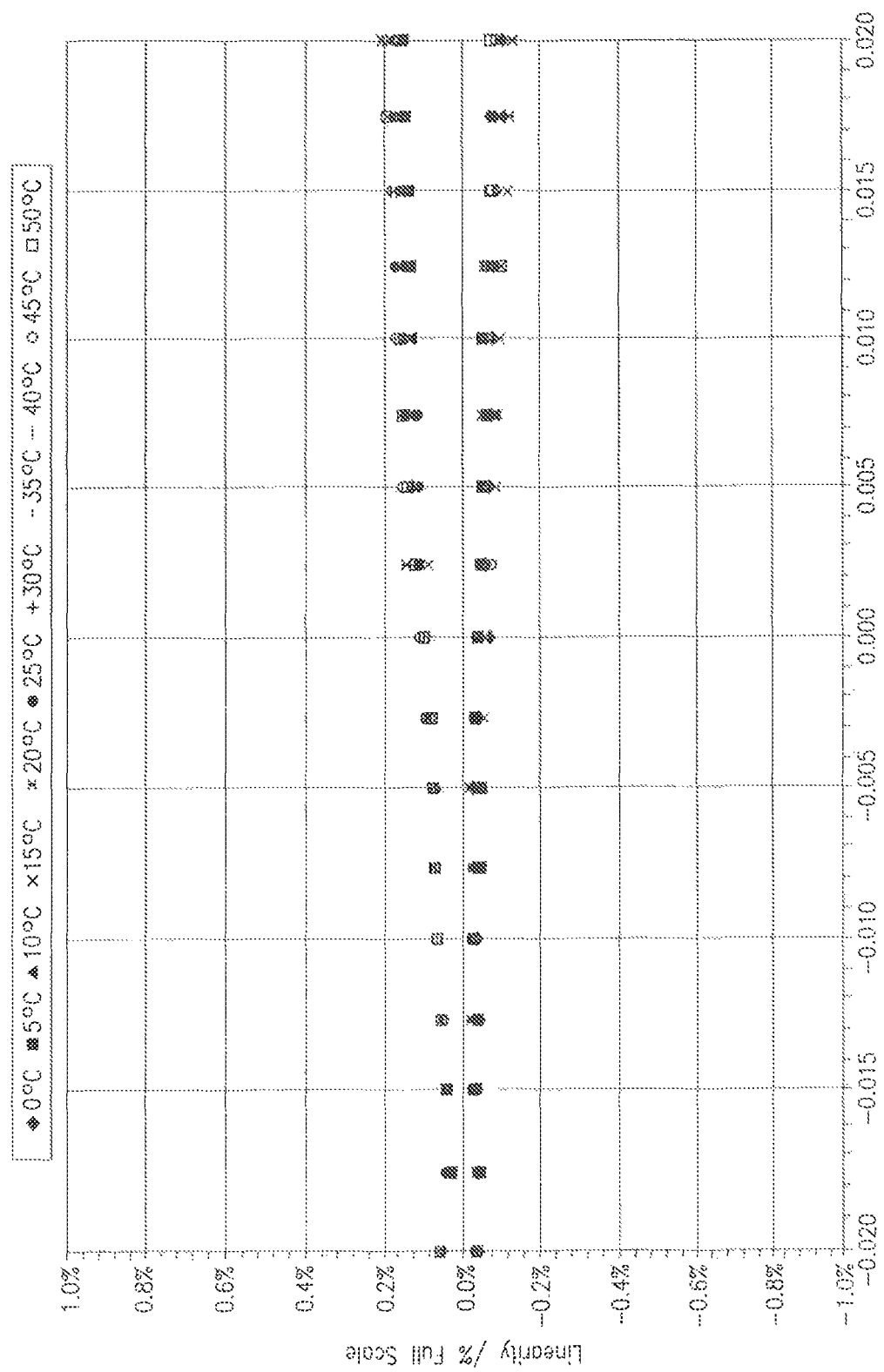
Figure 14:
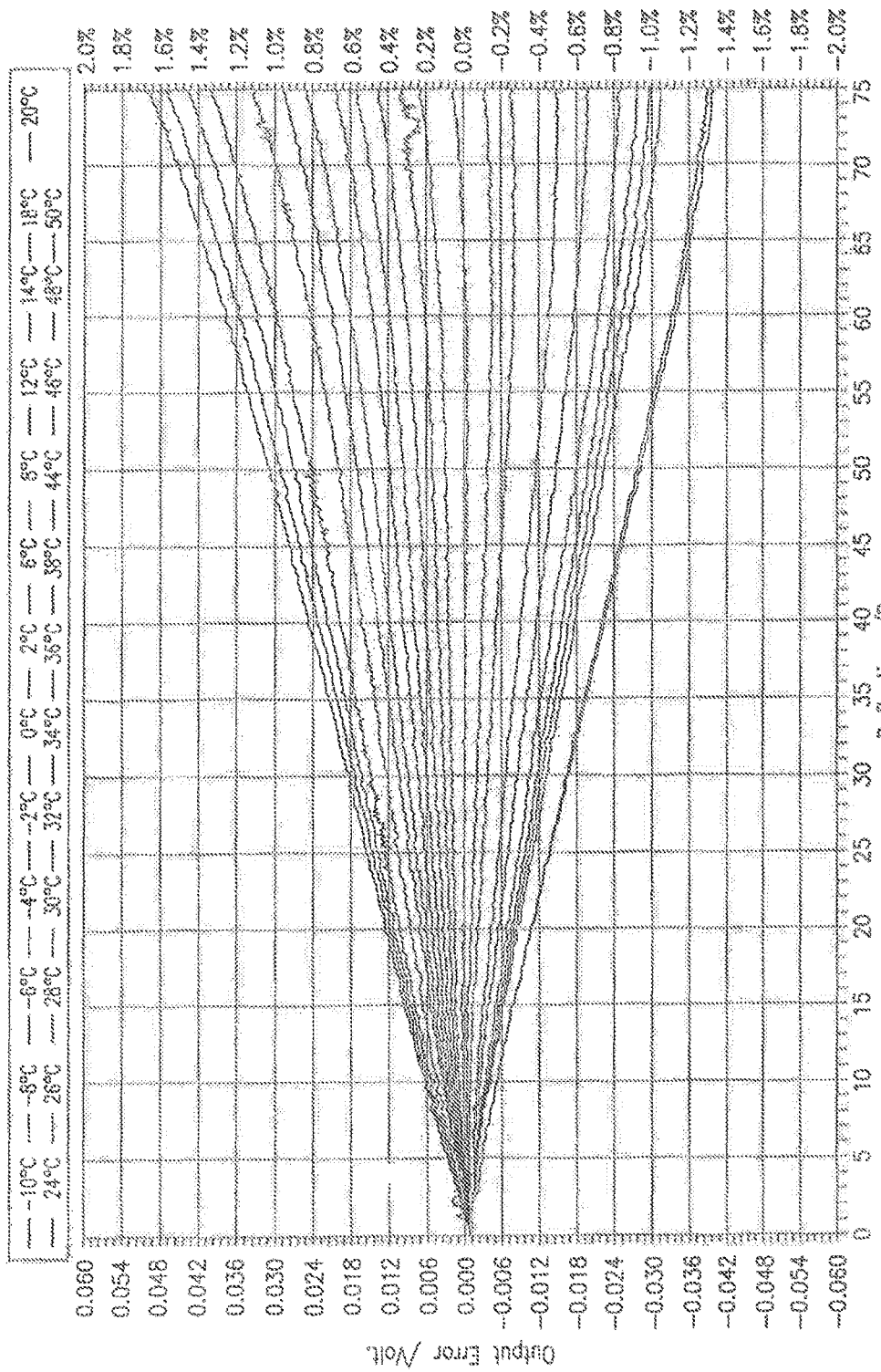

(c) error vs. x axis displacement (in range of −0.02 to +0.02 in per inch for the viscometer with Hall Effect transducer vs. for the viscometer with MSI transducer) (FIGS. 8 and 9); and (d) similar improvement comparisons for limits on error due to y, z axis deviations (FIGS. 10-13). The AS5045 sensor pulse width modulation output was used effectively to gain a substantial improvement.

The Hall Effect sensor and a conforming viscometer can operate with the same supply voltage level as existing instruments. The viscometer with the Hall Effect transducer is not sensitive to axial movement between the sensor and magnet over a significant amount of displacement, which is an advantage over other transducer types currently being used in this application. Since these transducers can be designed and internally compensated for temperature variations they are less affected by temperature than many conventional transducers. Also, low rotation speed not available for the viscometer below 5 rpm with the optical time base sensing mechanism is enabled by usage of the Hall Effect transducer down to about 0.01 rpm, with frequent (essentially continuous) readings of angular displacement not dependent on rotation speed.

The present invention includes use of other forms of large deflection angle accommodation magnetic transducers, in addition to Hall Effect transducers, e.g. rotary variable differential transformer (RVDT), such as the Pickering transducers found in early models of the BEL DV-1 and DV-2 digital viscometers. Also, details of the viscometer could be varied consistent with the present invention known per se, e.g. optical read-out for signal extraction, instead of the brush and slip ring option cited above.

It will now be apparent to those skilled in the art that other embodiments, improvements, details, and uses can be made consistent, with the letter and spirit of the foregoing disclosure and within the scope of this patent.

The invention claimed is:

1. A rotational instrument for measuring viscosity and/or rheological properties of a fluid medium comprising,
a driving rotational assembly, a driven rotational assembly with parts of the two rotational assemblies being disposed via coupling means in an operative compliantly coupled relationship such that a fluid medium can be placed to interact with the driving and driven rotational assemblies, wherein
the interaction between the assemblies being affected by fluid, shear stress and/or yield and varying as a function of viscosity and/or rheological properties,
a read-out component of the instrument comprising a multi-part Hall Effect device comprising a multi-sensor array to effect multiple forms of sensing signals, on a single die or substrate, with electrical drive means and electrically driven magnet and magnetic field sensing parts that produce an extractable electrical signal modulated by varying level magnetic field in the separate sensing parts and magnetic part, based on fluid characteristics, at the sensors, and means for extracting the signal, the magnetic field sensing parts having a sensing array coordinated with angular position of the magnet,
one of the parts connected to one of said driving or driven assemblies and the other part to the other of the assemblies and arranged in close proximity to detect angular deflection based on effect of the fluid between the assemblies in the course of their mutual rotation,
the Hall Effect device parts being in a common thermal environment.

2. The instrument of claim 1 wherein the driving and driven assemblies comprise driving and driven solid or hollow shafts or cylinders coupled to each other by at least one spiral spring to effect the compliant coupling.

3. The instrument of claim 2 wherein the respective driving and driven shafts or cylinder elements are coupled by two oppositely spiraled spiral springs.

4. The instrument of claim 1, wherein the compliant coupling is effected by a torsion wire.

5. The instrument of claim 1 wherein the compliant coupling is effected by a flexure means.

6. The instrument of any of claims 2-5 further comprising axially spaced centering means selected from the group consisting of bail or roller bearings, point jewel hearings, combination along a common length of the driving and driven shafts or cylinders, and operatively connected to both, and constructed to minimize bearing torque drag therebetween.

7. The instrument of claim 1, wherein the extraction means comprises brush and slip ring means.

8. The instrument of either of claims 1 or 7 wherein the extracting means comprises means to effect an initial digital output from the sensors, conversion of the output to an analog form including low pass filter means to reduce output ripples, but being insensitive to viscometer control circuit impedance to thereby reduce temperature sensitive drifts from leakage currents.

9. The instrument of claim 1, wherein the coupling means comprise an optical coupling.

10. The instrument of claim 1 wherein the coupling means comprise a torsion wire.

11. The instrument of claim 1 wherein the coupling means comprise a flexure means.

12. The instrument of claim 1 wherein the two parts of the Hall Effect device have a common axis of magnet and sensing array parts.

13. The instrument of claim 1 wherein the two parts of the Hall Effect device have offset axes of magnet and sensing array parts.

14. A rotational instrument for measuring viscosity and/or rheological properties of a fluid medium comprising;
   a driving rotational assembly; and
   a driven rotational assembly with parts of the two rotational assemblies being disposed in an operative compliantly coupled relationship such that a fluid medium can be placed to interact with the driven rotational assemblies, wherein
      the driving connection between the assemblies is affected by fluid, shear stress and/or yield and varies as a function of viscosity and/or rheological properties,
      a read-out component of the instrument comprising a multi-part magnetically coupled device with magnet and magnetic field sensing parts, the magnetic field sensing parts having a sensing array coordinated with angular position of the magnet,
      one of the parts connected to one of said driving or driven assemblies and the other part to the other of the assemblies and arranged in close proximity to detect angular deflection based on effect of the fluid between the assemblies in the course of their mutual rotation,
      the magnetically coupled device parts being in a common thermal environment.

15. The rotational instrument of claim 14, wherein the sensing array of the magnetic field sensing parts confronts the magnet.

* * * * *